United States Patent [19]

Keller

[11] Patent Number: 4,996,435

[45] Date of Patent: Feb. 26, 1991

[54] OPTICAL SYSTEM FOR TRANSMITTING DATA BETWEEN A STATIONARY PART AND A ROTATING PART

[75] Inventor: Walter Keller, Erlangen, Fed. Rep. of Germany

[73] Assignee: Siemens Aktiengesellschaft, Berlin and Munich, Fed. Rep. of Germany

[21] Appl. No.: 451,800

[22] Filed: Dec. 18, 1989

[30] Foreign Application Priority Data

Feb. 6, 1989 [EP] European Pat. Off. ............ 89102032

[51] Int. Cl.$^5$ .............................................. G02B 27/00
[52] U.S. Cl. ...................................... 250/551; 455/605
[58] Field of Search ......................... 250/551; 307/311; 455/602, 605, 603; 340/870.27, 870.28, 870.29

[56] References Cited

U.S. PATENT DOCUMENTS 4,175,230 11/1979 Richards et al. ............... 340/870.28
4,555,631 11/1985 Martens ................................. 455/602
4,854,662 8/1989 Estes et al. ........................... 250/551

Primary Examiner—David C. Nelms
Assistant Examiner—Que Tan Le
Attorney, Agent, or Firm—Hill, Van Santen, Steadman & Simpson

[57] ABSTRACT

An optical system for transmitting data between stationary part and a rotating part, such as for transmitting data from the rotating live ring in a computer tomography apparatus, has a number of light transmitter arranged on a circle on one of the parts, with the radiation output of the light transmitters being modulated according to the data to be transmitted, and a light receiver disposed on the other part. The light transmitters emit thin, fan-shaped light beams, each of the light beams being in a plane which is defined by the circle, or parallel thereto. Each fan-shaped light beam has a central ray disposed at an angle relative to a radius of the circle, and the light receiver is disposed relative to the circle and the light transmitters so that the light receiver is within the light beam of at least one light transmitter at every position of the rotating part, and thus supplies a constant output signal, given a constant transmitted signal, during rotation.

3 Claims, 3 Drawing Sheets

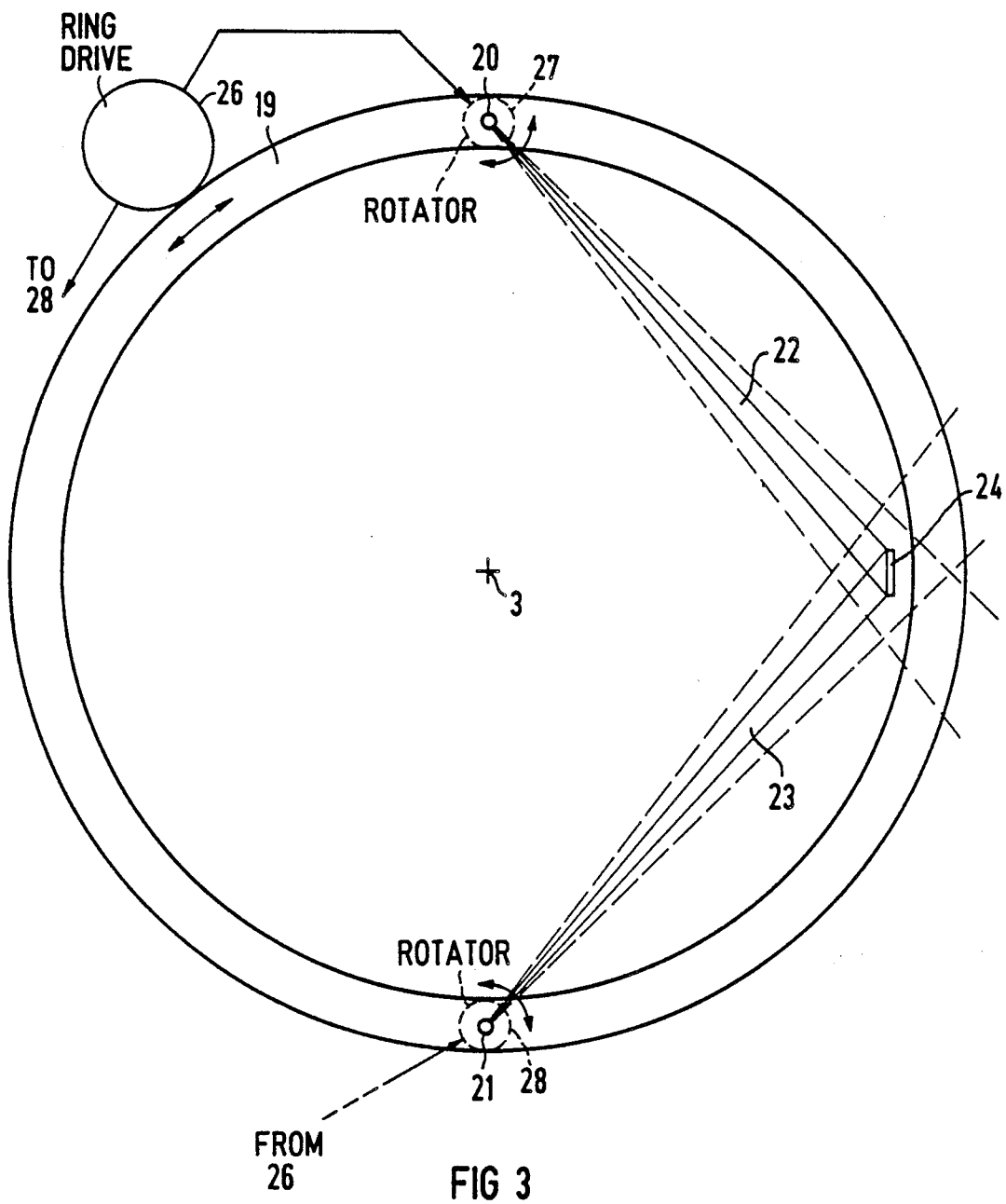

OPTICAL SYSTEM FOR TRANSMITTING DATA BETWEEN A STATIONARY PART AND A ROTATING PART

BACKGROUND OF THE INVENTION

1. Field of the Invention

The present invention is directed to an optical data transmission system for transmitting data between a rotating part and a stationary part, such as for transmitting data between the live rotating ring of a computer tomography apparatus and the stationary frame part of the apparatus.

2. Description of the Prior Art

In an apparatus having a rotating part and a stationary part, it is known to use a plurality of light transmitters mounted on the rotating part to transmit data, encoded in the output light of the transmitters, to a light receiver mounted on a stationary part. Such a system is disclosed for rotary machines in general in Research Disclosure No. 165, January 1978, page 5 No. 16503, Havant G. B.

In computer tomography devices, it is known to provide a row of light transmitters on one part and a row of light receivers on the other part, with the spacings of the light transmitters and the light receivers being selected so that a continuous data transmission ensues between the rotating part and stationary part.

SUMMARY OF THE INVENTION

It is an object of the present invention to provide a simplified structure for optical data transmission between a stationary part and a rotating part, which is less expensive than known systems.

The above object is achieved in accordance with the principles of the present invention in an optical transmission system wherein the light transmitters, mounted on one of the parts, emit thin, fan-shaped light beams, each beam being in a fan plane which is in the plane defined by a circle on which the transmitters are mounted, or in a plane parallel to the plane containing the circle. The light beam generated by each transmitter has a central ray, with the central rays of the respective light beams being disposed at respective angles relative to a radius of the circle extending from the center of the circle to the associated light transmitter. The orientation of the light transmitters and the light receiver is such that the light receiver "sees" at least on light transmitter at every position of the data transmission system, and thus supplies a constant output signal given a constant transmitted signal during rotation. Only one light receiver is used in the data transmission system, which permits disturbance-free data transmission in combination with a plurality, such as four, rotating light transmitters.

In a further embodiment of the invention, only two light transmitters are required, with each light transmitter being rotatable around an axis parallel to the rotational axis of the rotating part, the rotation of the rotating part and of the light transmitters are synchronized so that the light beams respectively emitted by the light transmitters keep the light receiver within the fan-shaped beam of a light transmitter, so that the angle which the central ray of the beam makes with the radius leading to the light transmitter varies.

DESCRIPTION OF THE DRAWINGS

FIG. 3 shows a further embodiment of an optical data transmission system constructed in accordance with the principles of the present invention.

DESCRIPTION OF THE PREFERRED EMBODIMENTS

Figure 1:
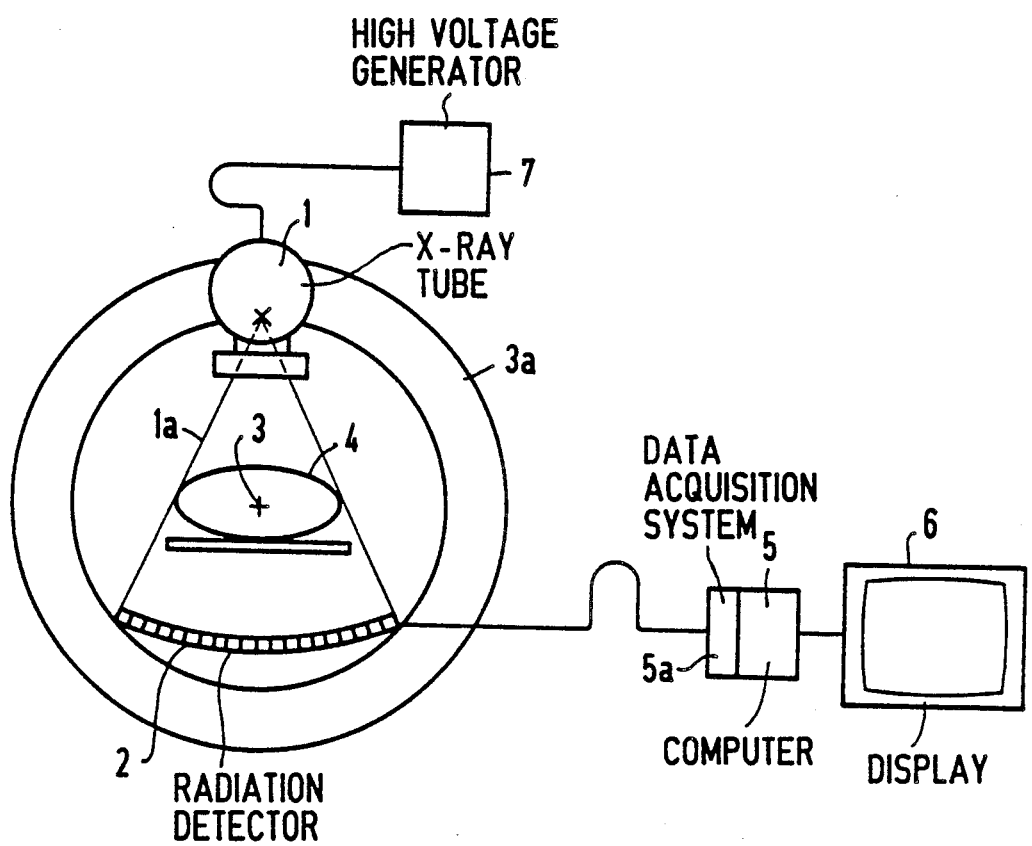
FIG. 1 is a schematic block diagram of a known computer tomography apparatus of the type in which the optical data transmission system constructed in accordance with the principles of the present invention can be used.

A computer tomography apparatus is shown in FIG. 1, of the type in which an optical data transmission system constructed in accordance with the principles of the present invention can be used. The tomography apparatus includes an x-ray tube which is fed by a high voltage generator 7. The x-ray tube 1 generates a fan-shaped x-ray beam 1a which penetrates an examination subject 4. Radiation attenuated by the examination subject 4 is incident on a radiation detector 2 which consists of over 100, for example 512, individual detectors arranged in a row. The fan-shaped x-ray beam 1 has a cross-sectional extent perpendicular to the slice plane which is equal to the slice thickness, and is of such a size in the slice plane that the entire examination subject 4 is penetrated by radiation. The radiation detector 2 is curved around the focus of the x-ray tube 1.

The x-ray tube 1 and the radiation detector 2 are mounted on a live ring 3a, which rotates around an axis 3 which is substantially coincident with the longitudinal axis of the examination subject 4. The number of detectors in the radiation detector 2 is selected corresponding to the desired image resolution. The radiation detectors 2 convert the incident radiation into electrical signals, which are supplied to a data acquisition system 5a. As is known, the data acquisition system 5a contains amplifier circuits, multiplexers, and analog-to-digital converters for each channel.

The output of the data acquisition system 5a is supplied to a computer 5, which constructs an image based on the electrical signals from the radiation detector 2. The resulting image is reproduced on a display 6.

An especially fast production of a plurality of tomograms of the examination subject 4 is possible when energy is transmitted from the high voltage generator 7 to the x-ray tube 1 via wiper rings, and the data from the detector elements of the radiation detector 2 are transmitted to the data acquisition system 5a via a rotating data transmission system. A continuous rotation of the live ring 3a, and thus a rapid, successive scanning of a plurality of slices of the examination subject 4, are then possible.

Figure 2:
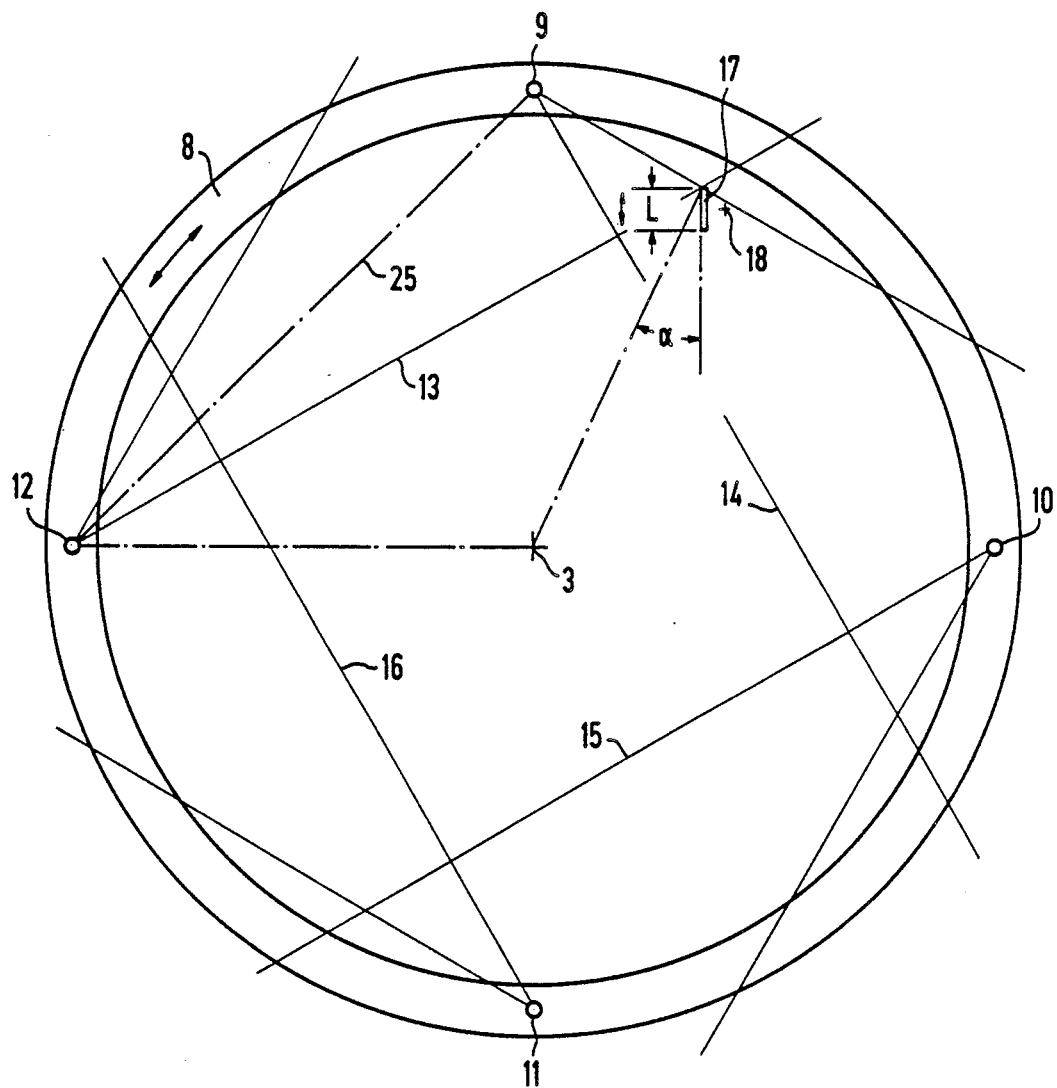
FIG. 2 shows a first embodiment of an optical data transmission system constructed in accordance with the principles of the present invention.

An optical data transmission system for non-contacting transmission of the data from the detector elements of the radiation detector 2 is shown in FIG. 2. The data acquisition system includes a frame 8, which is attached to and rotates with the live ring 3a. Four light transmitters 9, 10, 11 and 12 are symmetrically mounted on the frame 8. The light transmitters 9-12 respectively emit thin, fan-shaped light beams 13, 14, 15 and 16, which are modulated in a known manner with the information to be transmitted. The light beams 13-16 are incident on a light receiver 17, which is an optoelectrical transducer, and which supplies the received data to the data acquisition system 5a. The light receiver 17 has a rectangular, light-sensitive surface having a longitudinal extent L. The longitudinal extent L makes an angle α with a radius of the frame 8 which is selected so that the light receiver 17 "sees" at least one of the light transmitters 9-12 at every position of the frame 8. Given a constantly transmitted signal during rotation of the frame 8, the light receiver 17 thereby emits a constant output signal. A disturbance-free information transmission thereby is achieved, despite the changing spacings between the light transmitters 9-12 and the light receiver 17, and the relative alignment of these components with respect to one another. The light receiver 17 is pivotable around an axis 18, parallel to the axis 3, so as to be adjustable for this purpose.

The fan-shaped light beams 13-16 are each disposed in a fan plane, with the fan planes of the light beams being within, or parallel to, the plane defined by the frame 8.

In the embodiment of FIG. 2, a disturbance-free data transmission is achieved using four light transmitters 9-12 and a single light receiver 17. In the embodiment of FIG. 3, only two light transmitters 20 and 21 are required.

As shown in FIG. 3, the two light transmitters 20 and 21 are mounted on a rotating frame 19. The light transmitters 20 and 21 emit respective thin, fan-shaped light beams 22 and 23. As in the embodiment of FIGS. 2, the fan planes of the light beams 22 and 23 are in a plane defined by the frame 19, or parallel thereto. A light receiver 24 having a rectangular reception face is arranged so that the reception face is perpendicular to a radius of the frame 19. The frame 19 is rotated by a ring drive 26. (Such a ring drive is also present in the embodiment of FIG. 2, but is not needed to explain that embodiment.) The light transmitters 20 and 21 are mounted on respective rotators 27 and 28. Each of the rotators 27 and 28 is operated synchronously with the ring drive 26, so that the light beams 22 and 23 follow the light receiver 24 as the frame 19 is rotated. This synchronous operation can ensue electrically or by a suitable mechanical linkage. The rotation of the light transmitters 20 and 21 is selected so that the light receiver 24 always "sees" at least one of the light transmitters 20 and 21 during a full revolution of the frame 19. If, for example, the frame 19 is rotated in a clockwise direction, the light transmitter 21 can also be rotated in a clockwise direction around its axis parallel to the axis 3, so that the light beam 23 remains directed onto the light receiver 24.

In both of the embodiments of FIGS. 2 and 3, the respective central rays of the light beams 13-16, or 22 and 23, describe an acute angle with the radius extending through the associated light transmitter, so that the light receiver 17, or the light receiver 24, always has light incident thereon from at least one light transmitter 9-12, or 20 or 21. This angle is shown in FIG. 2 for the central ray 25 of the light beam 13.

Although modifications and changes may be suggested by those skilled in the art, it is the intention of the inventor to embody within the patent warranted hereon all changes and modifications as reasonably and properly come within the scope of his contribution to the art.

I claim as my invention:

1. An optical data transmission system for transmitting data between a rotating part and a stationary part comprising:
   a plurality of light transmitters arranged on a circle on said rotating part, each light transmitter emitting a thin, fan-shaped light-beam in a fan plane disposed in a plane defined by said circle or a plane parallel thereto, and each of said fan-shaped light beams having a central ray defining an angle with a radius of said circle intersecting an associated light transmitter; and
   a light receiver disposed on said stationary part relative to said light transmitters so that light from at least one light transmitter is incident on said receiver at every position of said rotating part so that, given constant transmitted signals from said light transmitters during rotation of said rotating part, said light receiver generates a constant output signal.

2. An optical data transmission system as claimed in claim 1, wherein said rotating part has a rotational axis, and further comprising:
   means for mounting said light receiver adjustably around an axis parallel to said rotational axis.

3. An optical data transmission system as claimed in claim 1, wherein said rotating part has a rotational axis, and further comprising:
   means for rotating said rotational part; and
   means for respectively mounting each of said light transmitters so as to be rotatable around respective axes parallel to said rotational axis and synchronized with said means for rotating said rotating part so that said respective light beams from said light transmitters follow said light receiver during rotation of said rotating part.

* * * * *